United States Patent [19]

Carroll et al.

[11] Patent Number: 4,640,785

[45] Date of Patent: Feb. 3, 1987

[54] SEPARATION OF LYMPHOCYTES AND MONOCYTES FROM BLOOD SAMPLES

[75] Inventors: Richard J. Carroll, Syracuse, N.Y.; Albert A. Luderer, Marshfield, Mass.; Ward C. Smith, Painted Post; Anthony R. Zine, Jr., Corning, both of N.Y.

[73] Assignee: Becton Dickinson and Company, Paramus, N.J.

[21] Appl. No.: 685,801

[22] Filed: Dec. 24, 1984

[51] Int. Cl.⁴ .............................................. B01D 21/26
[52] U.S. Cl. ..................................... 210/782; 210/789; 435/2
[58] Field of Search ................... 210/782, 789, 927; 435/2; 436/826

[56] References Cited

U.S. PATENT DOCUMENTS

| | | | |
|---|---|---|---|
| 3,852,194 | 12/1974 | Zine, Jr. .................... | 210/789 |
| 3,920,549 | 11/1975 | Gigliello et al. ............ | 210/789 |
| 4,101,422 | 7/1978 | Lamont et al. .............. | 210/927 X |
| 4,190,535 | 2/1980 | Luderer et al. ............. | 210/789 |
| 4,310,430 | 1/1982 | Ichikawa et al. ............ | 210/782 X |
| 4,435,293 | 3/1984 | Graham, Jr. et al. ........ | 210/782 X |
| 4,436,631 | 3/1984 | Graham, Jr. et al. ........ | 210/782 X |

FOREIGN PATENT DOCUMENTS

| | | | |
|---|---|---|---|
| 1127537 | 7/1982 | Canada ........................ | 210/782 |
| 0036168 | 9/1981 | European Pat. Off. ........ | 210/927 |

Primary Examiner—Richard V. Fisher
Assistant Examiner—W. Gary Jones
Attorney, Agent, or Firm—Hoffman, Dilworth, Barrese & Baron

[57] ABSTRACT

This invention is directed to means for inhibiting the apparent shift in the buoyant density of and/or to restore any loss in the buoyant density of the granulocytic white blood cells in a sample of blood, thereby insuring the quality of the separation of lymphocytes and monocytes from granulocytes in a blood sample. The invention comprises contacting a blood sample with a hypertonic fluid containing a low molecular weight organic or inorganic ionic substance and/or with an isotonic or hypertonic fluid containing a high molecular weight organic substance which may contain organic molecules having a lipophilic substituent in their structures and/or with a culture medium for blood cells. An integral part of the invention is an improved blood separation tube utilizing a gel-like substance having a specific gravity between 1.060–1.065 g/cm³ to significantly enhance the purity of cell separation, while providing acceptable cell yields.

13 Claims, 2 Drawing Figures

SEPARATION OF LYMPHOCYTES AND MONOCYTES FROM BLOOD SAMPLES

BACKGROUND OF THE INVENTION

U.S. Pat. No. 3,852,194 provides a general description of a process for separating lighter phases present in blood samples from heavier phases therein by means of a thixotropic, gel-like material having a specific gravity intermediate that of the phases to be separated. The gel and blood sample are centrifuged together and, during that operation, the gel flows sufficiently to form a barrier between the phases to be separated. The barrier allows the phase resting thereupon to be removed utilizing conventional laboratory techniques.

The patent suggests the utility of a wide variety of gel-like substances; three criteria therefor being cited as required attributes for those materials:

(a) a specific gravity intermediate to the phases desired to be separated;

(b) chemical inertness with respect to the phases desired to be separated; and (c) essentially non-flowable (semi-rigid) when at rest.

U.S. Pat. No. 3,920,549 discloses a modification of and an improvement upon the process of U.S. Pat. No. 3,852,194; the improvement involving the use of a solid element having a specific gravity greater than that of the gel-like substance. During centrifugation, the solid element, termed an "energizer", impacts upon the gel, which is commonly placed in the bottom of a blood collection tube, and thereby facilitates the upward movement of the gel along the walls of the tube. In so doing, the energizer hastens the separation of the blood fractions and enables a cleaner separation between the phases.

U.S. Pat. No. 4,190,535 is explicitly directed to means for extracting lymphocytes, monocytes, and platelets from anticoagulated blood. Three basic process steps are involved:

(1) a water-insoluble, thixotropic gel-like substance that is chemically inert to blood components and exhibits a specific gravity between about 1.065–1.077 g/cc is placed into a sample of anticoagulated blood;

(2) the gel-blood sample is centrifuged at a force of at least 1200 G's for a sufficient length of time to cause the gel-like substance to form a barrier between the heavier blood cells and the plasma, platelets, lymphocytes, and monocytes; and, thereafter, (3) the plasma, platelets, lymphocytes, and monocytes are withdrawn from atop the barrier.

The patented method is stated to comprise an improvement upon the separation technique widely used at that time. Thus, the then-conventional means for extracting lymphocytes and monocytes from anticoagulated human blood contemplated buoyant density centrifugation of cells for about 30–40 minutes at about 400–500 G's utilizing Ficoll-Paque ®, a Newtonian liquid having a specific gravity of 1.077 g/cc marketed by Pharmacia Fine Chemicals AB, Uppsala, Sweden. The use of Ficoll-Paque ® fluid, however, was accompanied by several problems:

(a) if, during the initial pipetting of the blood sample onto the Ficoll-Paque ® liquid, white cells are accidentally deployed below the surface of that liquid, the reduced specific gravity of the "load" Ficoll-Paque ® is inadequate to separate the lymphocytes and monocytes;

(b) if, during centrifugation, lighter phases in the blood are carried into the Ficoll-Paque ® medium, they may not ascend therethrough because of the low buoyant force generated by the 400–500 G's;

(c) centrifugation forces greater than about 400–500 G's cannot be employed because Ficoll-Paque ® liquid is somewhat water soluble and greater centrifugation speeds enhance the solubility thereof in blood, thereby leading to a reduction in its specific gravity;

(d) upon completion of centrifugation, withdrawal of the lymphocytes and monocytes from atop the Ficoll-Paque ® fluid must be carried out with great care because of the Newtonian character of the fluid; and (e) because the separation technique required at least one hour to complete, a less time-consuming process was desired.

By utilizing a thixotropic, non-Newtonian, water-insoluble gel-like substance capable of forming a barrier at centrifugation forces of in excess of 1200 G's, the method disclosed in U.S. Pat. No. 4,190,535 provided a faster separation process and a more complete separation than possible with the Ficoll-Paque ® fluid.

Long term studies of the extraction of mononuclear cells (lymphocytes and monocytes) from human blood samples using the gel separation tube have indicated that the performance quality of the separation is a function of the time which has elapsed since the blood sample was drawn. Hence, whereas quantitative recoveries of mononuclear cells at purities $\geq 85\%$ are observed on freshly drawn blood, after a relatively short lapse of time following blood draw, the recovered cells approach an unseparated total white cell population.

Figure 1:
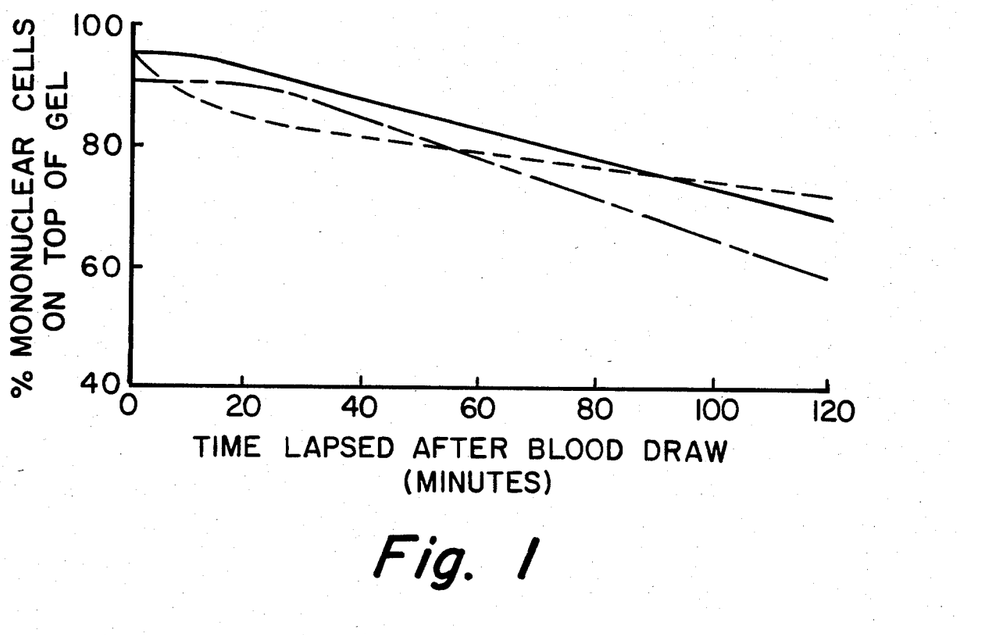
FIG. 1 comprises a graph illustrating the decrease in cell density over a period of time at constant ambient temperature.

This phenomenon is demonstrated by an increased contamination of the mononuclear cells resting atop the gel barrier with granulocytes as the period of time after the blood draw is extended. FIG. 1 illustrates the effect of time on the performance quality of the separation process on three different blood samples, reported in terms of the percent of mononuclear cells recovered atop the gel barrier after a 10-minute centrifugation at 1400 G's. As can be observed, pure mononuclear cells are obtained with freshly drawn blood samples, but after a time span of only 30 minutes, the purity of the cells dropped noticeably; and after only 2 hours the loss of purity was quite significant. As can be appreciated, such relatively rapid decay in performance can be of serious consequence to the patient. For example, an accurate measure of white blood cells, especially lymphocytes, is critically necessary for histocompatibility determinations. An indication of lymphocyte function is demanded where the type and level of medication needed for immunosuppression must be determined.

Figure 2:
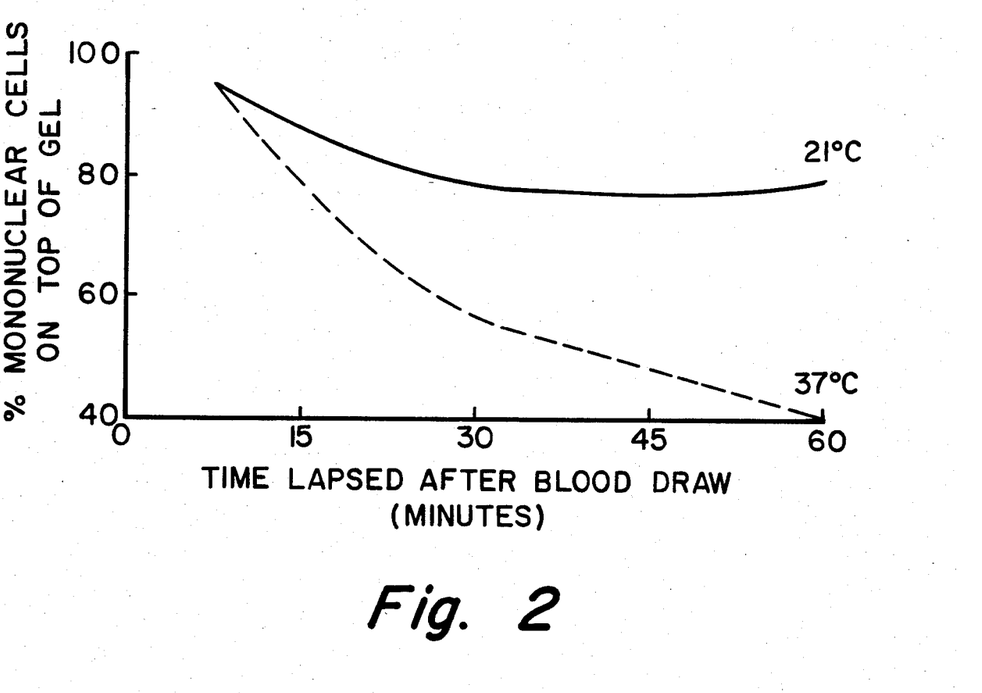
FIG. 2 comprises a graph illustrating that the extent of the decrease in cell density is a function of temperature.

FIG. 2 illustrates that the shift in buoyant density is accelerated at higher temperatures. Thus, the curves in FIG. 2 represent determinations of mononuclear cells carried out on two samples of the same blood, but at different temperatures, utilizing the same gel and process variables as discussed above with respect to FIG. 1.

The inability to recover pure mononuclear cells on aged blood appears to be independent of the gel-like substance used as a barrier, and is believed to represent an apparent shift in the buoyant density of the granulocytes.

Observation of a variety of normal and abnormal blood samples indicates a wide variability in density of cells within a given cell type density population. In fact, mathematical consideration of the density only profile of blood cell samples moving under theoretical conditions at sedimentation velocity through plasma would show a Gaussian distribution of each cell type over its density population range, with granulocytes overlapping trailing erythrocytes, lymphocytes overlapping trailing granulocytes, and monocytes overlapping trailing lymphocytes.

There are several ways in which cell density overlapping could be expected to increase. In vitro aging is one way in which overlapping of cell types occurs. Since typical cell densities are averages of many individuals, one would expect that samples on the extremes of normal distribution would show significant overlap. Certainly, pathologic examples would be expected to change cell population overlap and, in fact, do shift whole populations. These conditions can be expected to have a significant impact on variability in separation performance.

The mechanism responsible for density and volume shift of blood cells has been studied extensively. It is founded in three principal aspects of transport through cell membranes; viz., diffusion, facilitated transport, and active transport. Those transport systems are complex with various independent pathways which may be activated or blocked by different drugs. The $Na^+K^+$ pump is one such transport system.

A shift in osmolarity of the cell environment leads to the transport of ions into or out of the cell resulting in an obligatory change in water volume. This change in water volume constitutes the primary influence on cell size and density change. A detailed description of cell volume regulation is provided in "Biochimica Et Biophysica Acta", 774 (1984) pages 159–168, Elsevier Science Publishers Bv. In chapter 7 of a publication by IRL Press, "Iodinated Density Gradient Media", edited by Dr. D. Rickwood, there is an extensive description of the technology and methods of density gradient liquid cell separation. It is shown there that a 10% increase in osmolarity will theoretically cause a 2.2% decrease in cell radius in concert with a 0.4% increase in cell density. Dr. Rickwood describes the use of Nycodenz® and NaCl to control separation media density and osmolarity independently. Nycodenz® is the trademark name for a density gradient medium marketed by Accurate Chemical and Scientific Corporation, Westbury, N.Y., having a molecular weight of 821 and a density of 2.1 g/ml. The chemical systematic name therefor is N,N'-Bis (2,3-dihydroxypropyl)-5-[N-(2,3-dihydroxypropyl)acetamido]-2,4,6-triiodo-isophthalamide. The use of this medium to separate monocytes from lymphocytes is described, as well as the change in purity of monocytes as osmolarity is increased. A sedimentation gradient was used.

In the separation of cells utilizing liquid gradient media, three types of gradients are used. The first is a sedimentation gradient. Because of variations in sedimentation rates, in a given time one group of cells to be separated collects at the bottom of the tube while the second remains in the supernatant liquid. The second and third separation types are buoyant density gradients. Of these, the first is a discontinuous gradient. The sample is laid on top of the gradient. After sedimentation, one group of cells sits on top of the gradient liquid and the other in or beneath the density gradient. The second buoyant density gradient is called a continuous gradient. In this medium centrifugation causes the large molecules in the medium to move toward the bottom of the medium causing a continuous density gradient. Cells in this medium take up positions in the gradient according to their densities. Here one would expect density population overlap as described above.

Lymphocytes play a major part in the body's immune system. They are harvested and used in a major part of the research activity directed at defining the chemistry and physiology of immune mechanisms. For example, they comprise an important part of cancer and autoimmune disease research and are fundamental to monoclonal antibody technology. In many cases, contamination of lymphocytes by granulocytes and red cells makes the sample of cells unuseable due to chemical cross reactivities. For this reason, lymphocyte separation methods must produce purities routinely in excess of 90%.

It has been discovered that the mechanism of gel separation is fundamentally different from conventional buoyant density separation. Thus, in the former the gel is displaced from the bottom of the tube under centrifugal force by the mass of red cells which, when compacted, approaches a density of 1.09 g/cc. The gel, having a density of about 1.065–1.077 g/cc, is moved up the tube by buoyant force as the packed cell mass grows. The gel finally settles at a position where the suspension of cells approximates the density of the gel. That is, at a level where the combination of red cells, white cells, and plasma exhibits a density equal to or substantially equivalent to that of the gel.

At that equilibrium position the elongated gel mass is supported from below through the buoyant force of the mass of red cells. The suspension of cells at the top of the gel mass is less dense then the gel mass. This circumstance results in compression of the gel due to its weight under centrifugation. This compression forces the gel inwardly toward the center of the tube such that the mass assumes a more or less hourglass configuration. The rate at which the gel mass contracts or closes and the extent thereof is governed by the velocity of the cell gradient.

When sealing of the gel occurs, the stream of cells is attenuated, frequently with a thin stream of cells trapped in the gel mass, thereby forming, in essence, a marble. Plasma trapped underneath the gel tends to form a bubble as the cells compact below the gel and, if of sufficient size, will force its way up through the gel and produce a "hot lava pattern" on the surface of the gel. The gel then settles to replace the space left by the plasma.

One can mathematically approximate the conditions under which gel closure may occur; i.e., the conditions under which the buoyant forces of the cell gradient fall below the buoyant forces compressing the gel. At equilibrium those forces are equal. If the fact that the system is acting over a gradient is ignored, the concept can be simplified. Thus, in so doing the sum of the products of the densities and percent volumes of the phases present can then be equated. Red cells have a nominal density of about 1.10 g/cc, white cells a density of about 1.075, plasma a density of about 1.027, and the gel a density of about 1.065. Two boundary conditions can be defined utilizing the above values; one being all white cells and the second being all red cells. Accordingly:

For only plasma and white cells:
$1.075(x) + 1.027(1-x) = 1.065$ (1)
Where $x = \%$ white cells $= (1.065 - 1.027) \div (1.075 - 1.027) = \sim 0.79 = \sim 79\%$ white cells For only plasma and red cells:
$1.10(x) + 1.027(1-x) = 1.065(1)$ Where x=% red cells=(1.065−1.027)÷(1.10−1.027)=∼0.52=∼52% red cells Therefore, where a gel having a density of about 1.065 g/cc is employed, that gel will close on a cell suspension stream having a packed cell volume of about 50–80% in plasma, depending upon the mix of cells in the suspension. Obviously, a change in gel density will alter the boundary conditions.

An equation can also be developed to mathematically approximate the terminal velocity of a spherical particle moving under gravitational forces in a viscous liquid. The equation is operative only for single particles, however. Such an equation indicates that the velocity is a direct function of the density difference between the particle and the medium, a direct function of the square of the particle diameter, and an inverse function of the viscosity of the medium. Nevertheless, if this equation were to be applied to each cell type, the predicted result would be found to be somewhat opposite to the sequence occurring in actual separation of the phases. Thus, in the actual separation process the red cells appear to be first.

This phenomenon has been explained in the observation that the suspension of cells is so dense that mass cell streaming occurs with many red cells acting in mass with the equivalent diameter of the mass. It has been deemed likely that the red cells are first and last. That is, first because of a clumping and mass effect, and last because, as the cell suspension thins out during the separation, the individual cells move in accordance with the above equation such that the smallest cells arrive last. Hence, the front end of the cell suspension gradient moves under different influences than the trailing end thereof. Consequently, substantial red cell contamination must be expected.

As the suspended cells approach the packed cell mass, the larger cells, which inherently move more rapidly than the smaller cells, begin to slow down due to the increasing density of the cell suspension. At a red cell concentration of about 60%, the density of the suspension approaches that of lymphocytes. Such a stream is sufficiently dense to support the gel opening, so white cells can be expected to slow down or even reverse direction, according to their densities, while still in a position above the gel and before the gel closes. Large numbers of red cells traveling downward at this stage of the separation process can be expected to pile up onto those white cells, thereby tending to oppose this action. This behavior may also explain, at least in part, some of the red cell contamination inasmuch as the white cells would, in turn, hold up the red cells. That is, the cells would begin to form layers according to the densities of the individual phases. Accordingly, in this sense the concentrated cell suspension begins to act as its own density separation gradient. The gel closes before equilibrium can be reached, but not before substantial density separation occurs.

When the density of the gel is increased, it can be expected to position itself lower in the tube, resulting in closure occurring sooner because of increased compression forces. This action is evidenced through the greater yield of cells as the density of the gel is increased. To illustrate, yields can be as low as 15–20% with a gel having density of 1.055 g/cc, but at 70–80% with a gel having a density of 1.08 g/cc. This advantage in yield can be lost where high purity of phase separation is desired, since the purity of the separated lymphocytes acts in reverse. Therefore, an optimum choice must be made between the two parameters. And in view of the above discussion, it is believed evident that applications demanding that the purity of the majority of samples be above 90% cannot be satisfied by varying only the physical properties of the gel.

Once the gel is sealed, the individual cells do not have sufficient density to displace the gel. Hence, as the cells move out of the plasma (density ∼1.027 g/cc) and into the gel (density ∼1.065), the relative density of the cell becomes negligible. The viscosity of the gel, being about 100,000 times that of plasma, further reduces cell velocity. Accordingly, a cell that travels two inches in plasma in a few minutes would require several days to sink to the depth of its own diameter into the gel. Stated in another way, the gel comprises a door which closes, thereby leaving cells above it available for removal. Such cells constitute a lymphocyte-rich mixture of red and white cells.

Unlike conventional liquid density separation media, the gel medium does not act on individual cells in a buoyant density separation but, instead, assumes a position in the tube based upon the average buoyant density of a changing cell gradient in suspension; in essence acting as a door closing on a sedimentation gradient. Both because of the relative velocities of the cell types and the buoyant density effect of the cells themselves, the cells resting upon the top of the gel are lymphocyte-rich. Red cell contamination can be removed through lysing. Purification requires the addition of chemical agents to supplement the separation activity of the gel.

Inasmuch as individual cells do not reach buoyant density equilibrium, it is believed that cell diameter may exert a significant influence on the gel medium separation because of the diameter squared parameter in the above-discussed velocity equation. However, since the cell mass and the concentrated cell suspension are in motion, it is difficult to judge when velocity effects are replaced by buoyant density effects. Furthermore, assessment of the effect of red cell capturing which prevents white cells from rising against the stream of descending red cells is not easy. It is known that aging causes an increase in the diameter of cells, especially granulocytes, and that a forced reduction in cell size significantly improves the separation of aged blood samples. Hence, aging effects can effect changes in diameter five times greater than a change in density; density decreasing as the cell becomes larger. For example, a 2.2% change in diameter will result in a 5% change in cell sedimentation velocity.

When diameters of typical blood cells are reviewed, it will be observed that the granulocyte range falls within the lymphocyte range and the monocytes overlap the high end of the granulocyte range. The diameters of red cells are about equivalent to those of the smallest lymphocytes. Hence, there is considerable overlapping in the ranges of cell diameters. Consequently, the fact that a reasonably substantial separation occurs indicates that, because of the near coincidence of cell diameters, the densities of the cells, wherein there is much less overlap, must play a very significant role in the gel separation process. Therefore, it appears evident that velocity controls sedimentation profiles and constitutes a primary initial mechanism of the separation process, whereas during the later portion of the separation process, i.e., when the cell concentration gradient is high and still above the gel closure position, density comprises the more dominant separation mechanism.

Where a cell suspension is composed predominantly of red cells, it becomes its own separation gradient medium.

It is possible to alter the osmolarity of the plasma through the use of chemical agents to change cell diameters and cell densities. Thus, the cells of a given cell type can be moved toward the center of population of that cell type, thereby reducing the range of density. That movement has the effect of thinning the extent of overlapping of the cell populations. For example, the larger lymphocytes which lead the lymphocyte sedimentation profile can be drawn back toward the lymphocyte center of population. The small, trailing granulocytes will not be significantly influenced since such a hyper-osmotic chemical treatment is less effective on small dense cells. At the same time, however, the density of large granulocytes will be so modified as to move them toward the center of the granulocyte population. This latter action becomes important at the conclusion of the separation process where buoyant density effects would otherwise cause the large granulocytes to be forced upward out of the mass of red cells. The overall result is that lymphocytes are held back and granulocytes facilitated down the tube during the separation process through the use of a density/size adjusting reagent. In sum, because the cell types are given greater separation distance, the gel can close with fewer granulocytes trapped in the lymphocyte population, thereby leading to improved purity.

The above chemical treatment can reverse the detrimental effects of sample aging as well as improving the separation of "difficult" samples. In like manner hypo-osmotic treatment can be utilized to enlarge cells. This practice may have a short-lived effect, however, due to the volume regulatory ability of the cells. Moreover, this treatment is also more disruptive to the cells.

OBJECTIVE OF THE INVENTION

The primary objective of the instant invention is to optimize the performance of the gel separation method by (1) modification of the gel and (2) the use of reagents to treat the blood sample prior to separation. Whereas the reagent treatment is operable with liquid separation techniques, the preferred practice is that described in U.S. Pat. No. 4,190,535.

SUMMARY OF THE INVENTION

It is not surprising that the density of the gel described in U.S. Pat. No. 4,190,535 has a range of 1.065–1.077. With the wide variability of cell densities, use of freshly drawn blood and use of EDTA anticoagulant, fair results can be obtained. This range of densities would be considered inclusive, if one considered that the principal competitive liquid method utilized a density of 1.077 (which approximately matches the density "window" between granulocyte and lymphocyte population profiles), and operation of the gel was anticipated to separate individual lymphocytes on the basis of buoyant density. In fact, there is a tendency for the gel to seal early based on the lower density of a cell suspension comprising red and white cells in plasma. Experimental work on two gel types indicates that optimum performance of the gel may be in the density range of 1.060–1.065. This range of densities for optimum separation of lymphocytes is outside the expectation of those skilled in this area of technology. In fact, it has not been obvious what the true nature of the separation mechanism is. Acceptable purities can be obtained in gels with densities as low as 1.055. The choice of densities in the 1.060–1.065 range results in the gel sealing later in the passage of granulocytes through the sealing area. Gels above this density range tend to increase yield, but at the cost of lower purity, of mononuclear cells. Typically, gels in the 1.060–1.065 range give better yields than a liquid density gradient medium and so slightly lower densities which sacrifice some yield to improve purity are acceptable.

Some researchers have expressed concern that yields of lymphocytes below 50% may lead to the preferential separation of certain sub-populations, such shifts in sub-populations hazarding erroneous diagnostic and/or research conclusions. Hence, there is a minimum value below which the density of the gel may negatively impact upon cell sample preparations.

A second aspect of the invention comprises the treatment of a sample of whole blood with a reagent which causes the cells to expel water, thereby increasing the density and decreasing the size thereof. Inasmuch as the lighter cells in each cell density population are most affected by such treatment, the forward cells in the sedimentation profile experience a decrease in velocity and move toward the center of the density population of each cell type. Also, in the later stages of the separation process when buoyant density effects result from red cell concentration, the large granulocytes which have decreased in size and increased in density are facilitated down the tube away from the lymphocyte population, resulting in a decrease in overlap between granulocyte and lymphocyte populations. As the gel closes on this thinning population of cells, more lymphocytes and fewer granulocytes are captured. Finally, this treatment inhibits the effects of blood aging which renders blood samples increasingly difficult to separate, especially in gel separation techniques.

Several mechanisms control molecular transport across cell membranes and, therefore, several different reagent approaches may be taken to control density/volume. Thus, at the simplest level, the addition of hyperosmotic reagents, such as hypertonic sodium chloride solution, to the suspension will shift osmolarity and cause water to move out of the cells. The transport mechanisms through which that phenomenon occurs are not fully understood. For purposes here it is sufficient to say that the cells have volume regulating capabilities which may be activated or blocked. The $Na^+K^+$ pump is one such mechanism.

In any event, chemicals which actually change osmularity and/or trick the cells into thinking osmularity has changed can be used. Furthermore, chemicals which block volume change recommend themselves to deter the effects of blood aging. Combinations of those reagents can impart complementary behavior. The cost of salt is negligible when compared with density gradient media. Hence, the use of NaCl in conjunction with a chemical medium such as Nycodenz ® can reduce overall cost.

In addition to Nycodenz ® density gradient medium, we have found the following other iodinated organic compounds having a lipophilic substituent to be useful as gradient density compounds. Metrizoic acid [3-acetamido-5-(N-methylacetamide)-2,4,6-tri-iodobenzoic acid] with a molecular weight of 628 forms the basis of a family of compounds exhibiting the desired character. Two especially useful derivatives of metrizoic acid are the sodium salt thereof, viz., sodium metrizoate, and metrizamide, a complex compound having a molecular weight of about 789 which is defined as 2-(3-acetamido-5-N-methylacetamide-2,4,6-triiodobenzamido)-2-deoxy-D-glucose. Both of those materials are marketed by Accurate Chemical and Scientific Corporation, Westbury, N.Y.

Isotonic aqueous solutions of the above-described organic molecules are effective in restoring the density of granulocytes. Nevertheless, it has been observed that hypertonic solutions of those materials operate more rapidly. Therefore, where speed of action is essentially the sole criterion, hypertonic solutions of those molecules can be employed although, as can be appreciated, the cost of the separation will be increased.

In summary, the inventive methods are designed to maintain the purity or quality of lymphocytes and monocytes from samples of anticoagulated human blood via the use of a gel separation medium by inhibiting the apparent shift in the buoyant density of the granulocytic white blood cells. Gels for use in the separation tube are preferably selected with densities well below the expected density range for separation of mononuclear cells and outside the density range of U.S. Pat. No. 4,190,535. This unexpected condition results from the novel way in which gels position and seal which has not been previously understood. The preferred gel density range which balances both cell purity and cell yield is 1.060–1.065 g/cc. While gel tubes of this design offer fair performance, consistently high purities are not predictable. Use of EDTA has an effect in improving the purities over other anticoagulants. However, for many applications heparin is the preferred anticoagulant, and in many cases purity falls below acceptable levels.

A second inventive step is required in the form of reagent treatment of the samples. In broad terms, the inventive incubation process contemplates contacting a sample of blood with a hypertonic fluid containing a low molecular weight ionic substance which is essentially chemically compatible with the cells and/or with an isotonic or hypertonic fluid containing high molecular weight organic molecules which are essentially chemically compatible with the cells and may contain a lipophilic substituent in their structure for a sufficient length of time, i.e., generally longer than about 1 minute and typically at least 10 minutes, to return the buoyant density of the granulocytes to approximately their original level. The inclusion of either or both of those fluids inhibits the shift in buoyant density depicted in FIGS. 1 and 2. The separation of lymphocytes and monocytes from the granulocytes may then be carried out in the conventional manner utilizing a gradient separation medium, most desirably a water-insoluble, thixotropic gel-like substance such as is described in U.S. Pat. No. 4,190,535 discussed above.

Whereas close control is difficult to achieve, it is possible to incorporate a required amount of the hypertonic fluid containing a low molecular ionic substance and/or the isotonic or hypertonic fluid of high molecular weight organic molecules into the separation medium to produce the desired shift in buoyant density as the separation process is in progress.

Accordingly, the preferred practice utilizes the above-described incubation or pretreatment step and the separation process will comprise the four basic elements:

(a) a fresh or aged anticoagulated blood sample is mixed with the hypertonic fluid containing a low molecular weight organic and/or inorganic ionic substance and/or the isotonic or hypertonic fluid containing a high molecular weight substance having molecules which may contain a lipophilic substituent, contact between said blood sample and said fluid being maintained for more than about 1 minute;

(b) a water-insoluble, thixotripic gel-like substance which is chemically inert to the constituents of said blood sample and said fluid is placed into the anticoagulated blood-fluid mixture;

(c) the blood-fluid-gel mixture is centrifuged at a force and for a sufficient length of time (typically at least about 10 minutes) to cause the gel-like substance to flow sufficiently to form a barrier between the lymphocytes and monocytes and the heavier blood cells; and then (d) the lymphocytes and monocytes are removed from atop said barrier.

Most desirably, the thixotropic gel-like substance utilized as the density separation medium will have a composition such as is disclosed in U.S. Pat. Nos. 3,852,194 and 4,190,535, a specific gravity between about 1.055–1.075 g/cm$^3$, and centrifugation will be conducted at a force of at least 1200 G's.

Also, it will be appreciated that, as explained in U.S. Pat. No. 4,190,535, the plasma fraction of the blood containing platelets will also rest upon and float above the barrier. The separation of the lymphocytes and monocytes from the plasma fraction containing platelets is described in U.S. Pat. No. 4,190,535 and that description is equally applicable here. Hence, in like manner to the general method for separating lymphocytes and monocytes from the heavier blood cells described in the prior art, the separation of lymphocytes and monocytes from the plasma fraction of blood containing platelets does not constitute inventive subject matter of the present process.

BACKGROUND LITERATURE

T. A. W. Splinter, M. Bendeker, and A. van Beek in "Changes in Cell Density Induced by Isopaque," *Experimental Cell Research* 3, 245–251 (1978) observed that, where mononuclear leucocytes, previously isolated from blood samples by means of Ficoll-Isopaque as the separating phase, were incubated in a culture medium at 37° C., the specific gravity of those cells decreased. The authors discovered that this decrease in cell density could be inhibited by performing the incubation at 0° C. or by adding Ficoll-Isopaque to the incubation medium. They also found that the decrease in mononuclear cell density resulting from incubation in a culture medium at 37° C. could be reversed by contact with Ficoll-Isopaque. Further investigation indicated that Isopaque was the agent responsible for shifting the density of the cells back toward their original specific gravity; which determination led the writers to the conclusion that the use of small molecular weight substances, such as Isopaque, as a constituent of density gradients may introduce reversible changes of the specific gravity of mononuclear leucocytes.

However, the authors did not disclose a general aging phenomenon in unseparated blood, nor, specifically, did they describe any effect on granulocytes. Their observation of a decrease in the buoyant density of lymphocytes previously isolated from blood samples is not a priori predictive with respect to any action of granulocytic white blood cells.

Dr. D. Rickwood, referenced above, pointed out that various iodinated compounds could effect an opposite change in density to the heavier side, and that such a change could promote an effective separation of monocytes from lymphocytes.

DESCRIPTION OF PREFERRED EMBODIMENTS

Whole human blood samples from five donors were drawn, utilizing conventional phlebotomy techniques, into the closed system lymphocyte separator tubes described by A. A. Luderer, A. R. Zine, D. M. Hess, J. N. Henyan, and G. Odstrchel, "Rapid, Quantitative Human Lymphocyte Separation and Purification in a Closed System", *Molecular Immunology*, 16, pp. 621–624 (1979). As is explained by those authors, a water insoluble, thixotropic gel chemically inert to blood constituents was formulated from a dimethyl polysiloxane and a precipitated methylated silica in which the methylation renders the material hydrophobic U.S. Pat. No. 4,190,535). The separator tubes were aseptically prepared by depositing gel on the bottom of sterile, siliconized glass test tubes containing sufficient lithium heparin to act as a coagulant followed by placing sterile polyester energizers (U.S. Pat. No. 3,920,549) in the center of the gel mass. Other known anticoagulants, e.g., EDTA, may be employed with equal facility. The separator tubes were then evacuated. Because the plastic energizer possesses a specific gravity greater than the gel, centrifugation forces the energizer through the gel, displacing gel up the walls of the test tube. This action, while not mandatory for satisfactory tube performance, facilitates separation and gel seal formation.

The use of the closed system separator tube minimizes problems in the handling of the blood samples. Nevertheless, the use of open tubes, such as is described in U.S. Pat. No. 4,190,535, is also operable. Also, other gel formulations have been found to perform in a similar manner. For example, gels modified from serum separation tube formulations, such as are described in U.S. Pat. Nos. 4,101,422 and 4,310,430, have demonstrated similar operability.

The blood samples were immediately placed into an unrefrigerated table top centrifuge and centrifuged at about 1400 G's for about 10 minutes to achieve equilibrium. The plasma fraction of the blood, which is enriched with platelets, plus the lymphocytes and monocytes ride upon the gel barrier mass, while the granulocytes and other heavier components of the blood are held below the barrier.

Thereafter, the plasma fraction was carefully extracted such that lymphocytes and monocytes comprise the predominant cells remaining on the gel barrier. An isotonic salt buffer solution was gently run into the tube and that liquid agitated by successive repipettings to resuspend the cells off the gel barrier. The so-formed cell suspension was withdrawn from the tube and the percentage of mononuclear cells retained on top of the barrier determined by counting 400 H & E (hematoxin and eosin) stained cells. Table I records those values.

Other human blood samples were drawn into tubes containing lithium heparin as an anticoagulant and diluted with the diluents recited in Table I. Merely as a matter of convenience, the dilution was in the ratio of 3 volumes of blood:1 volume of diluent. After the dwell times set out in Table I, the blood samples were separated and processed in the manner reported above with respect to the unaged blood samples. The specific gravity of each gel is also tabulated.

TABLE I

| Sample No. | Diluent | Time in Diluent |
|---|---|---|
| 1 | 0 | 0 |
| 1 | Saline Sol'n* | 24 hours |
| 1 | Saline Sol'n** | 24 hours |
| 1 | Metrizamide* | 24 hours |
| 1 | Metrizamide** | 24 hours |
| 2 | 0 | 0 |
| 2 | Saline Sol'n* | 24 hours |
| 2 | Saline Sol'n** | 24 hours |
| 2 | Metrizamide** | 24 hours |
| 3 | 0 | 0 |
| 3 | Saline Sol'n* | 24 hours |
| 3 | Saline Sol'n** | 24 hours |
| 3 | Saline Sol'n*** | 24 hours |
| 4 | 0 | 0 |
| 4 | Saline Sol'n* | 24 hours |
| 4 | Saline Sol'n** | 24 hours |
| 4 | Metrizamide* | 24 hours |
| 4 | Metrizamide** | 24 hours |
| 5 | 0 | 0 |
| 5 | Saline Sol'n** | 1 hour |
| 5 | Metrizamide** | 1 hour |
| 5 | Saline Sol'n** | 2 hours |
| 5 | Metrizamide** | 2 hours |
| 6 | 0 | 0 |
| 6 | Metrizamide** | 2 hours |
| 6 | Metrizamide** | 4 hours |

| Sample No. | % Mononuclear Cells Atop Barrier | Specific Gravity of Gel (g/cm$^3$) |
|---|---|---|
| 1 | 83 | 1.075 |
| 1 | 63 | 1.075 |
| 1 | 83 | 1.075 |
| 1 | 63 | 1.075 |
| 1 | 94 | 1.075 |
| 2 | 89 | 1.075 |
| 2 | 66 | 1.075 |
| 2 | 83 | 1.075 |
| 2 | 90 | 1.075 |
| 3 | 92 | 1.060 |
| 3 | 73 | 1.060 |
| 3 | 86 | 1.060 |
| 3 | 91 | 1.060 |
| 4 | 99 | 1.065 |
| 4 | 71 | 1.065 |
| 4 | 79 | 1.065 |
| 4 | 71 | 1.065 |
| 4 | 86 | 1.065 |
| 5 | 81 | 1.063 |
| 5 | 51 | 1.063 |
| 5 | 93 | 1.063 |
| 5 | 84 | 1.063 |
| 5 | 98 | 1.063 |
| 6 | 93 | 1.063 |
| 6 | 93 | 1.063 |
| 6 | 91 | 1.063 |

In Table I, saline solution* refers to a single aqueous isotonic NaCl solution. Saline solution represents a single NaCl solution which is hypertonic through having twice as much NaCl therein as the isotonic solution, and saline solution* is also hypertonic via the presence of three times the level of NaCl as the isotonic solution. Metrizamide* indicates an isotonic aqueous solution thereof, and metrizamide** designates an aqueous solution thereof which is hypertonic through containing twice as much of that ingredient as the isotonic solution.

When Table I is surveyed in conjunction with FIGS. 1 and 2, several conclusions can be drawn therefrom:

First, the specific gravity of granulocytes decreases relative to lymphocytes and monocytes as a blood sample ages, the rate of decrease being a function of time and temperature;

Second, the immersion of whole blood into an isotonic liquid containing a low molecular weight ionic substance has essentially no effect upon the specific gravity of the cells; and Third, the immersion of whole blood into a hypertonic liquid containing a low molecular weight ionic substance inhibits or reverses the decrease in specific gravity of the cells, the degree of inhibition or reversal being dependent upon the level of osmotic pressure of the hypertonic fluid.

The somewhat greater effectiveness of the hypertonic metrizamide solution, when compared with the hypertonic saline solution, has not as yet been fully explained. Three possible mechanisms therefor have been conjectured. The first is founded in differential osmotic activities of the two solutes. The second posits different interactions occurring between the two solutes with the osmotic regulatory element of the cell membrane. The third theorizes a potential interaction of the metrizamide molecules with the cell membrane which may confer increased specific gravity to the cell independent of osmotic considerations.

Furthermore, it has been recognized that the benzamide ring present in metrizamide, derivatives thereof, and related compounds imparts a significant lipophilic character to the molecule. Hence, it is postulated that the molecule may exhibit substantial plasma membrane solubility which permits it to more easily interact with the cell membrane. (It should be noted that the Nycodenz ® density gradient medium discussed above does not contain a benzamide ring and its effectiveness is not founded in organic molecules having a lipophilic substituent in their structures.)

Intracellular levels of [Na+] are positively regulated by the cells, themselves, by means of an energy dependent, plasma membrane bound Na+K+ pump. Hence, in the normal cell, intracellular [Na+] is maintained at a lower level than the extracellular [Na+]. Accordingly, the ingress of [Na$^{30}$] from the hypertonic saline solution is actively opposed by the cell.

In yet another embodiment of the inventive cell separation system, a culture medium for blood cells constitutes the reagent for inhibiting a shift in the buoyant density of and/or to restore loss in the buoyant density of granulocytes.

Cells in their natural environment live in a homeostatic system which provides for their normal growth. These cells in vitro tend to exhibit aging effects and eventually die due to the lack of such a system. Many types of cell media have been developed to support cell growth in vitro. Most typically, cells are separated and grown in a medium suspension of cells.

It has been found that the cell separation characteristics of whole blood can be preserved by adding a cell culture medium thereto. Whereas it is believed that any cell culture medium for blood cells will give positive results, Roswell Park Memorial Institute medium and McCoy's medium were particularly effective. For example, when whole blood samples were diluted with amounts of those media varying about 20-50% by volume, the purities of the separations were generally better than those achieved with hypertonic salt solutions and salt solutions with Hycodenz ®. Thus, purity performance shifts from about 83% to about 93% have been observed.

J. K. A. Nicholson et al. in "Comparison of T and B Cell Analyses on Fresh and Aged Blood", *Journal of Immunological Methods*, 73, pp. 29-40 (1984) describe the dilution of whole blood samples with a cell culture medium, specifically noting the use of McCoy's 5a medium. However, there was no disclosure by the authors that the addition of cell culture medium imparted any beneficial effect in the separation of lymphocytes from granulocytes. That is to say, the authors simply indicated a routine dilution of blood samples with no recognition or even an intimation that a cell culture medium can be utilized in the mode of the present invention; viz., not only as a diluent but also as a preservative for whole blood. No mention whatever is made of its utility in improving the separation of lymphocytes and granulocytes in a blood sample employing a gel-like substance in the inventive separation process.

It will be appreciated that, whereas the present invention is specifically directed to aged blood samples, the process is operable with fresh blood. Stated in another way, the inventive process insures a quantitative separation of lymphocytes and monocytes even where the lapse of time between blood draw and testing has been significant. Thus, the inclusion of a compatible, incubation fluid with fresh blood has no adverse effect upon the subsequent operation of lymphocytes and monocytes.

We claim:

1. A method for separating lymphocytes and monocytes from granulocytes in a sample of anticoagulated unseparated whole blood wherein an apparent shift in the buoyant density of the granulocytes is inhibited an any loss in buoyant density of the granulocytes is restored which comprises the steps of:
   (a) incubating said sample of anticoagulated unseparated whole blood with a fluid selected from the group consisting of a hypertonic fluid containing a low molecular weight organic ionic substance which is essentially chemically compatible with the blood cells, a hypertonic fluid containing a low molecular weight inorganic ionic substance which is essentially chemically compatible with the blood cells, an isotonic fluid containing a high molecular weight organic substance which is essentially chemically compatible with the blood cells, a hypertonic fluid containing a high molecular weight organic substance which is essentially chemically compatible with the blood cells, a culture medium for blood cells and combinations thereof, said incubation of said sample of anticoagulated unseparated whole blood with said fluid being maintained for a sufficient length of time to inhibit the apparent shift in the buoyant density of the granulocytes and restore any loss in the buoyant density of the granulocytes;
   (b) placing a water-insoluble, thixotropic gel-like substance which is chemically inert to blood constituents and said fluid into the blood-fluid mixture resulting from step (a);
   (c) centrifuging the blood-fluid gel mixture of step (b) at a force and for a sufficient length of time to cause said gel-like substance to flow sufficiently to form a barrier between the lymphocytes and monocytes and the granulocytes; and then (d) removing the lymphocytes and monocytes from atop said barrier.

2. A method according to claim 1 wherein said hypertonic fluid containing a low molecular weight ionic substance is an aqueous saline solution.

3. A method according to claim 1 wherein said ionic substance has a molecular weight of less than about 1500.

4. A method according to claim 1 wherein said high molecular weight organic substance contains molecules having a lipophilic substituent in their structure.

5. A method according to claim 4 wherein said high molecular weight organic substance is selected from the group consisting of metrizoic acid, derivatives thereof and combinations thereof.

6. A method according to claim 5 wherein said derivative of metrizoic acid is selected from the group of sodium metrizoate and metrizamide.

7. A method according to claim 1 wherein said high molecular weight organic substance is N,N'-Bis (2,3-dihydroxypropyl)-5-[N-(2,3-dihydroxypropyl)acetamido]-2,4,6-triiodo-isophthalamide.

8. A method according to claim 1 wherein said culture medium for blood cells is selected from the group of Roswell Park Memorial Institute medium and McCoy's medium.

9. A method according to claim 1 wherein said gel-like substance has a specific gravity between about 1.055–1.075 g/cm$^3$.

10. A method according to claim 9 wherein said gel-like substance has a specific gravity between about 1.060–1.065 g/cm$^3$.

11. A method according to claim 1 wherein said centrifuging is conducted at a force of at least 1200 G's.

12. A method according to claim 1 wherein said incubation of said sample of anticoagulated unseparated whole blood with said fluid is maintained for a time of from more than about 1 minute.

13. A method according to claim 1, wherein said incubation of said sample of anticoagulated unseparated whole blood with said fluid is maintained for a time of at least 10 minutes.

* * * * *

UNITED STATES PATENT AND TRADEMARK OFFICE
CERTIFICATE OF CORRECTION

PATENT NO. : 4,640,785
DATED : February 3, 1987
INVENTOR(S) : Carroll, et al.

It is certified that error appears in the above-identified patent and that said Letters Patent is hereby corrected as shown below:

Column 14, Line 3, delete "Hycodenz®" and insert --Nycodenz®--

Column 14, Line 38, before inhibited, delete "an" and insert --and--

Signed and Sealed this

Nineteenth Day of January, 1988

Attest:

DONALD J. QUIGG

*Attesting Officer*          *Commissioner of Patents and Trademarks*